US005518584A

United States Patent [19]
Aikawa

[11] Patent Number: 5,518,584
[45] Date of Patent: May 21, 1996

[54] DEVICE FOR DETECTING FOREIGN MATTER IN PULP SUSPENSION

[75] Inventor: Yoshihiko Aikawa, Shizuoka, Japan

[73] Assignee: Aikawa Iron Works Co., Ltd., Shizuoka, Japan

[21] Appl. No.: 121,248

[22] Filed: Sep. 15, 1993

[30] Foreign Application Priority Data

Jun. 28, 1993 [JP] Japan .................................. 5-157737

[51] Int. Cl.$^6$ ...................................................... D21B 1/00
[52] U.S. Cl. ............................ 162/49; 162/198; 162/263
[58] Field of Search ................................... 162/4, 49, 55, 162/198, 263; 356/442

[56] References Cited

U.S. PATENT DOCUMENTS

| | | | |
|---|---|---|---|
| 4,758,308 | 7/1988 | Carr | 162/263 |
| 4,863,107 | 9/1989 | Harzl et al. | 241/21 |
| 4,931,657 | 6/1990 | Houston et al. | 250/559 |
| 5,078,859 | 1/1992 | Satomi | 209/17 |
| 5,278,411 | 1/1994 | Popil et al. | 250/330 |

OTHER PUBLICATIONS

Lavigne, J. R. "Paper Industry Instrumentation", Miller Freeman Pub; 1977.

*Primary Examiner*—David L. Lacey
*Assistant Examiner*—Dean T. Nguyen
*Attorney, Agent, or Firm*—Kanesaka & Takeuchi

[57] ABSTRACT

An apparatus for detecting and determining the average value of the foreign materials contained in pulp suspension includes a pulp suspension introducing passage connected to a separating device including a primary chamber and a secondary chamber separated by a screen, the pulp components in the pulp suspension passage pass through the primary chamber, screen, and secondary chamber; a circulation passage connected between the primary chamber's inlet and outlet for circulating the pulp suspension containing the foreign materials in the primary chamber therethrough; and a device for detecting and determining the average value of the foreign materials contained in the circulated pulp suspension, the detecting device being located in the circulation passage.

5 Claims, 5 Drawing Sheets

DEVICE FOR DETECTING FOREIGN MATTER IN PULP SUSPENSION

BACKGROUND OF THE INVENTION

1. Field of the Invention

The present invention relates to a method of detecting foreign matter or materials in pulp suspension and a device for detecting the same.

2. Description of the Related Art

In a papermaking process, foreign matter or materials mixed with paper materials causes paper break (break deteriorates operational performance of a paper machine and increases in the production cost) and deteriorates the quality of paper as a commercial product, and consequently, foreign matter in pulp suspension is removed by using a screen, a cleaner, or the like. It is important to check the state of foreign matter in the pulp suspension (such as whether a large amount of foreign matter is present, or the like) which is fed to the papermaking process.

Thus, conventionally, the state of foreign matter, such as dust, contained in the pulp suspension is checked by the following method. The pulp suspension per se is extracted and a handmade sample sheet is produced from the extracted pulp suspension. Foreign matter in the sample sheet is counted, or foreign matter in paper as a finished product is counted.

However, in this method, feedback to the machine in the papermaking process is delayed, and thus, a quick response is not achievable.

In order to overcome the above drawbacks, the following method is available in these days. Light is ejected to the pulp suspension per se, and the resulting reflected light is detected and processed.

In such a method, approximately 1% concentration of the pulp suspension enables the detection of foreign matter such as dust, or the like.

However, when the pulp suspension is highly concentrated, it is difficult to distinguish foreign matter, such as dust, from effective fiber, thus lowering measuring precision.

If the pulp in the pulp suspension is bleached, the effective fiber and foreign matter in the pulp suspension can be distinguished by the difference of colors (the contrast of colors). However, when the pulp suspension material is waste paper, corrugated board, or the like, it is hard to distinguish foreign matter from effective fiber in the pulp suspension, thus lowering measuring precision.

SUMMARY OF THE INVENTION

Accordingly, an object of the present invention is to provide a method of detecting foreign matter or materials in pulp suspension in which sampled pulp suspension is diluted by adding water and the diluted pulp suspension is the object to be detected, and thus, foreign matter can be distinguished and detected easily and reliably regardless of the concentration of the pulp suspension which will be sampled; and to provide a device for detecting the same.

Another object of the present invention is to provide a method of detecting foreign matter in pulp suspension in which sampled pulp suspension is diluted by adding water and separated into foreign matter and effective fiber, and consequently, water containing the separated foreign matter is the object to be detected, thus distinguishing and detecting foreign matter easily and reliably regardless of the concentration of the pulp suspension which will be sampled, and even though the pulp suspension material is waste paper, corrugated board, or the like; and to provide a device for detecting the same.

A further object of the present invention is to provide a device for detecting foreign matter in pulp suspension in which the effective fiber and foreign matter in the sampled pulp suspension are discharged from a discharge passage and a foreign-matter discharge passage, respectively, and the pulp suspension to be newly sampled is introduced to separating means as a new object to be detected by opening introducing-passage opening and closing means, thus distinguishing foreign matter continuously.

DESCRIPTION OF THE PREFERRED EMBODIMENTS

Figure 1:
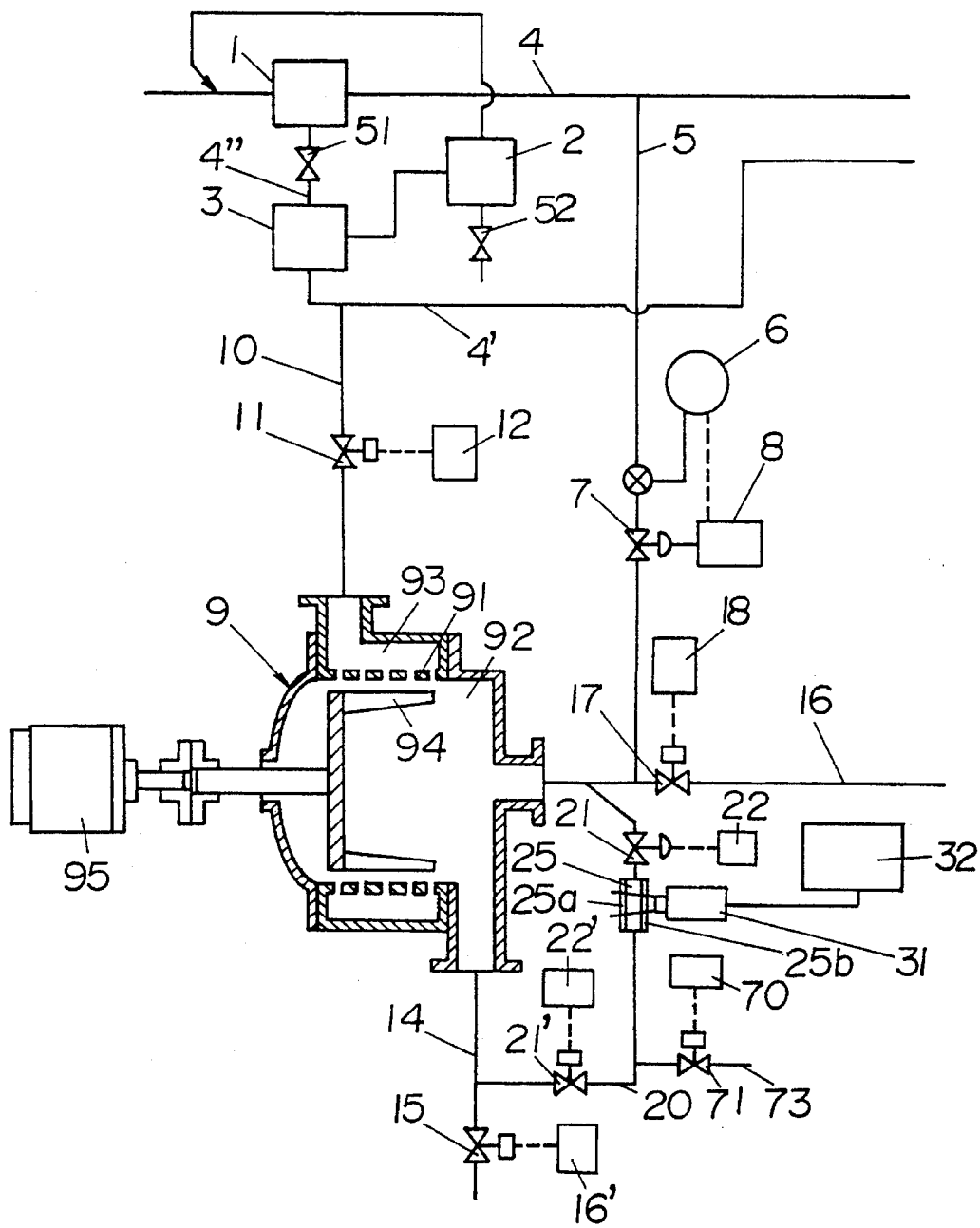
FIG. 1 is a schematic view explaining a device for detecting foreign matter in pulp suspension of one embodiment according to the present invention.

One embodiment of the present invention will be described with reference to the drawings. FIG. 1 shows a part of a process of adjusting papermaking materials. First and second screens 1 and 2 for removing foreign matter such as dust, or the like, from pulp suspension, and a tank 3 for storing the pulp suspension are connected to each other via pulp suspension passages 4, 4' and 4". Reference numerals 51 and 52 indicate valves.

A passage 5 for introducing the pulp suspension is connected to the pulp suspension passage 4 on the discharge side of the first screen 1, thereby introducing the pulp suspension to separating means 9.

A flow-rate integrating meter 6 and introducing-passage opening and closing means 7 (for example, an electromagnetic valve) are arranged in the passage 5 along the flow of the pulp suspension, thereby introducing a predetermined rate of the pulp suspension to the separating means 9. Introducing-passage opening and closing controls means 8 control the opening and closing of the introducing-passage opening and closing means 7. When the pulp suspension integrated in the flow-rate integrating meter 6 reaches a predetermined rate, a signal is transmitted to the introducing-passage opening and closing control means 8 so as to instruct the introducing-passage opening and closing means 7 to close.

The pulp suspension introducing passage 5 is connected at one end to the pulp suspension passage 4 on the discharge side of the first screen 1 as stated above and at the other end to the separating means 9.

The separating means 9 separates foreign matter or materials from the effective fiber in the pulp suspension and is partitioned into, for example, a primary chamber 92 and a secondary chamber 93 via a screen 91. A rotating member 94 rotated by a motor 95 prevents the screen 91 from being clogged.

A discharge passage 10 for discharging the effective fiber separated by the separating means 9 is connected at one end to the secondary chamber 93 of the separating means 9 and at the other end to the pulp suspension passage 4' connected to the tank 3.

Discharge-passage opening and closing means 11 (for example, an electromagnetic valve) opens and closes the discharge passage 10, and discharge-passage opening and closing control means 12 controls the opening and closing of the discharge-passage opening and closing means 11.

On the other hand, a foreign-matter discharge passage 14 for discharging foreign matter separated by the separating means 9 is connected to the primary chamber 92 of the separating means 9. Opening and closing means 15 (for example, an electromagnetic valve) for foreign-matter discharge passage is also connected to foreign-matter discharge passage 14 in order to open and close the foreign-matter discharge passage 14. Opening and closing control means 16' for the foreign-matter discharge passage controls the opening and closing of the opening and closing means 15 for the foreign-matter discharge passage.

A water-supply passage 16 for supplying water is connected to the primary chamber 92 of the separating means 9 with a view to diluting the pulp suspension, thus performing the separation easily by the separation means 9. Water-supply passage opening and closing means 17 opens and closes the water-supply passage 16. Water-supply passage opening and closing control means 18 further controls the opening and closing of the water-supply passage opening and closing means 17.

A circulation passage 20 is connected to the central portion and the side portion of the primary chamber 92 of the separating means 9, thus circulating water including the foreign matter present in the primary chamber 92 and stirring foreign matter so as to average the objects to be detected.

The circulation passage 20 is provided with circulation passage opening and closing means 21 and 21' (for example, electromagnetic valves) for opening and closing the circulation passage 20, and the opening and closing of the circulation passage opening and closing means 21 and 21' are further controlled by circulation passage opening and closing control means 22 and 22', respectively.

An inspecting section 25 for inspecting foreign matter (the inspecting section is formed of, for example, two pieces of transparent glass 25a and 25b parallel to each other) is arranged on the circulation passage 20 en route, and detecting means 32 is further provided for the detecting section 25.

The detecting means 32 detects reflected light of the light struck on the inspecting section 25 by using a CCD camera 31, thereby image-processing and detecting (measuring) foreign matter (the detecting means 32 is, for example, a dirt counter ASP-D400P made by Omron Corporation).

Also, a wash-water passage 73 is connected at one end to the circulation passage 20 en route in order to discharge the water, a small amount of fiber and foreign matter remaining in the primary chamber 92. Wash-water opening and closing means 71 is further arranged on the wash-water passage 73 en route, and wash-water opening and closing controls means 70 control the opening and closing of the wash-water opening and closing means 71.

Thus, when the pulp suspension is to be sampled, the introducing-passage opening and closing means 7 and the discharge-passage opening and closing means 11 are opened, thereby feeding the pulp suspension to the separating means 9 via the pulp suspension introducing passage 5. In this state, the rotating member 94 rotates.

After a certain amount of pulp suspension is fed to the separating means 9 by the flow-rate integrating meter 6, the introducing-passage opening and closing means 7 is closed by the introducing-passage opening and closing control means 8.

Subsequently, the water-supply opening and closing means 17 is opened, and a certain amount of water is supplied to the primary chamber 92 of the separating means 9 from the water-supply passage 16, thus diluting the pulp suspension. The diluted pulp suspension in the primary chamber 92 is stirred by the rotating member 94, and the resulting effective fiber flows out to the discharge passage 10 via the screen 91 and the secondary chamber 93. As a result, water, a small amount of fiber and foreign matter which cannot pass through the screen 91 remain in the primary chamber 92.

Figure 2:
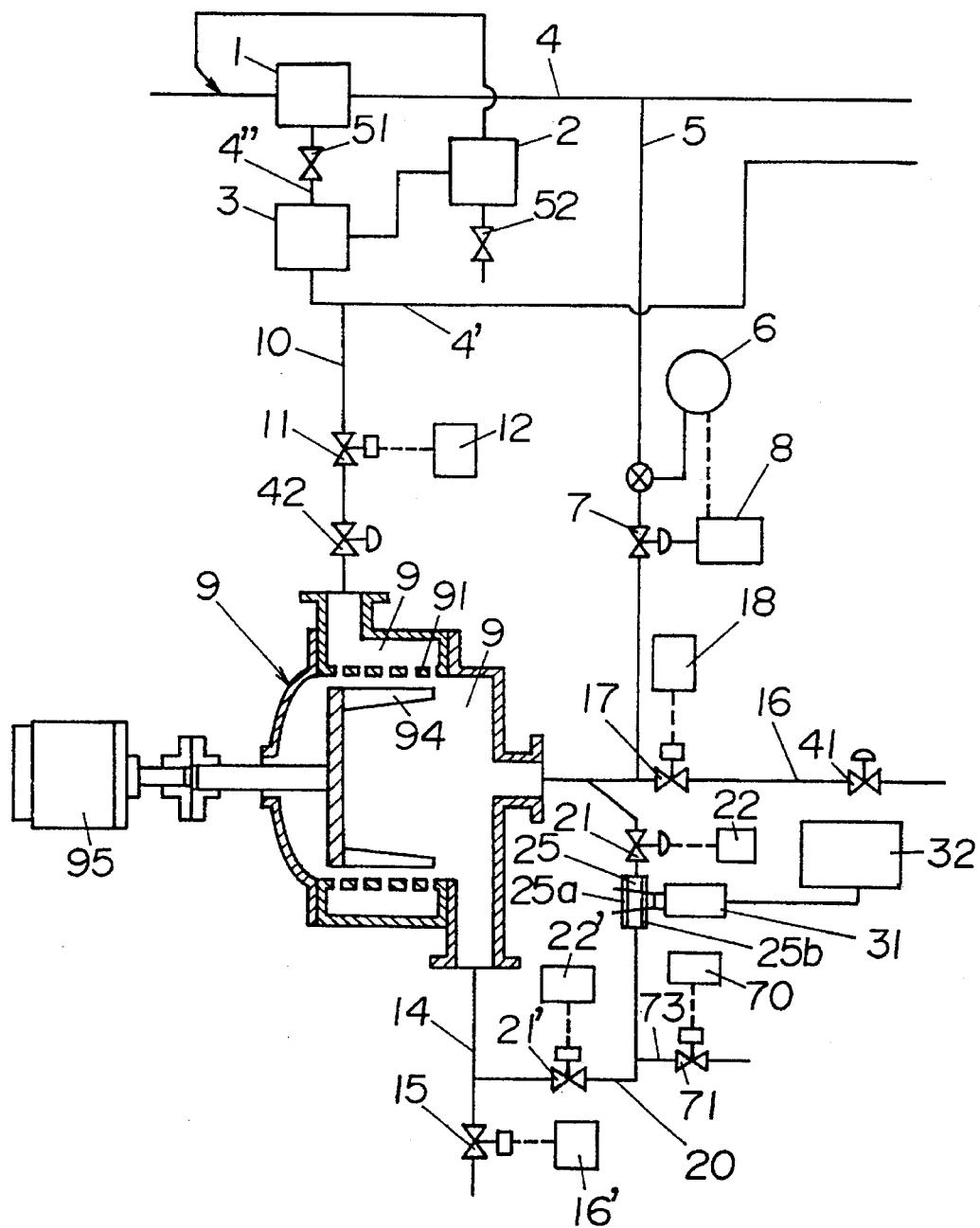
FIG. 2 is a schematic view explaining a device for detecting foreign matter in pulp suspension of another embodiment according to the present invention.

Then the water-supply opening and closing means 17 and the discharge-passage opening and closing means 11 are closed. The water-supply opening and closing means 17 and the discharge-passage opening and closing means 11 may be closed, but instead, as illustrated in FIG. 2, first and second flow-rate adjusting valves 41 and 42 arranged in the water-supply passage 16 and the discharge passage 10, respectively, may be throttled automatically or manually so that pressure required in the separating means 9 is maintained, thus supplying a certain amount of pulp suspension and water and preventing air from mixing into the separating means 9. Air mixed into the separating means 9 causes a problem for inspection in the inspecting section 25.)

Then the circulation-passage opening and closing means 21 and 21' are opened, and the water, a small amount of fiber and foreign matter remaining in the primary chamber 92 are circulated in the circulation passage 20 for a predetermined time by the rotating member 94, thus detecting foreign matter by the detecting (measuring) means 32.

That is, when light strikes the inspecting section 25, the resulting reflected light is detected by using the CCD camera 31 and image-processed by the detecting means 32, thereby detecting (measuring) foreign matter.

The circulation-passage opening and closing means 21' is closed, and the wash-water opening and closing means 71 is opened by the wash-water opening and closing control means 70 so as to wash the inspecting section 25. The opening and closing means 15 for foreign matter discharge passage is also opened so as to supply water via the wash-water passage 73, thereby discharging the water, a small amount of fiber and foreign matter remaining in the primary chamber 92 and waiting for the following detecting.

As described above, a predetermined pulp suspension in which the detected object is sampled is diluted with a certain amount of water so as to separate foreign matter from the effective fiber and to produce "water including separated foreign matter". Hence, it is possible to distinguish and detect foreign matter in the pulp suspension even though the pulp suspension is highly concentrated and the material thereof is waste paper, corrugated board, or the like.

According to the detection results, when a large amount of foreign matter in the pulp suspension is present, the rejecting volume of the screen (cleaner) of a main line is adjusted. For example, when a large amount of foreign matter is detected in the detecting section 25 after the pulp suspension is screened by the second screen 2 which is already screened by the first screen 1, the valves 51 and 52 are opened so as not to supply the pulp suspension screened by the second screen 2 to the first screen 1 but to supply it to another section via the pulp suspension passage 4'.

When a large amount of foreign matter is present in the pulp suspension as stated above, the improvement in dust removing efficiency in the material adjusting process is targeted in order to remove foreign matter as much as possible, and the foreign-matter mixing rate is observed, thus constantly supplying high-quality material to the paper machine, further obtaining good quality paper and preventing paper break.

In the embodiment shown in FIG. 1, the flow-rate integrating meter 6 and the introducing-passage opening and closing means 7 are used so as to introduce a certain amount of pulp suspension to the separating means 9. However, the present invention is not limited to this embodiment. Instead, for example, a flow-rate indicator may be used in lieu of the flow-rate integrating meter 6; or the function of a flow-rate control valve may be provided for the introducing-passage opening and closing means 7; or a timer may be integrated into the introducing-passage opening and closing control means 8 so as to close the introducing-passage opening and closing means 7 with the lapse of a predetermined time, thus introducing a certain amount of pulp suspension to the separating means 9.

Also, in this embodiment, although only the pulp suspension discharged from the first screen 1 is detected, the pulp suspension supplied to the first screen 1 may also be detected, and the results of detecting both pulp suspension may be compared and the dust-removing efficiency of the first screen 1 may be calculated. According to the calculation results, the discharge volume of the first screen 1 can be controlled.

Figure 3:
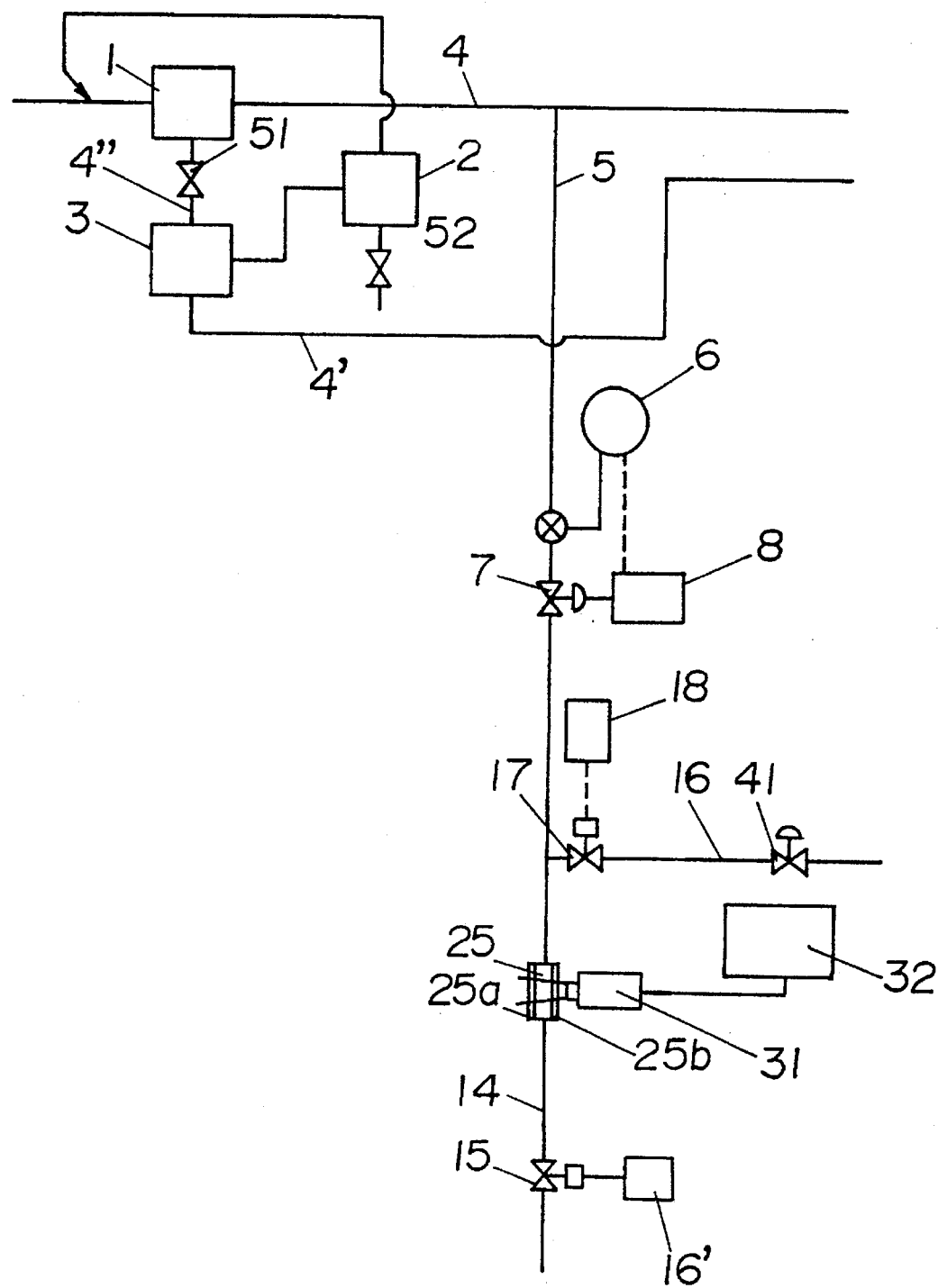
FIG. 3 is a schematic view explaining a device for detecting foreign matter in pulp suspension of another embodiment according to the present invention.

Further, in this embodiment, a certain amount of sampled pulp suspension is diluted by adding a certain amount of water and separated into foreign matter and effective fiber. Thus, water containing separated foreign matter is detected. However, the present invention is not limited to this embodiment. For example, as illustrated in FIG. 3, instead of arranging the separating means, a certain amount of sampled pulp suspension may be diluted (for instance, by opening the introducing-passage opening and closing means 7 for a predetermined time) by adding a certain amount of water (for instance, by opening a first flow-rate adjusting valve 41 for a predetermined time), and the resulting pulp suspension may be detected.

Figure 4:
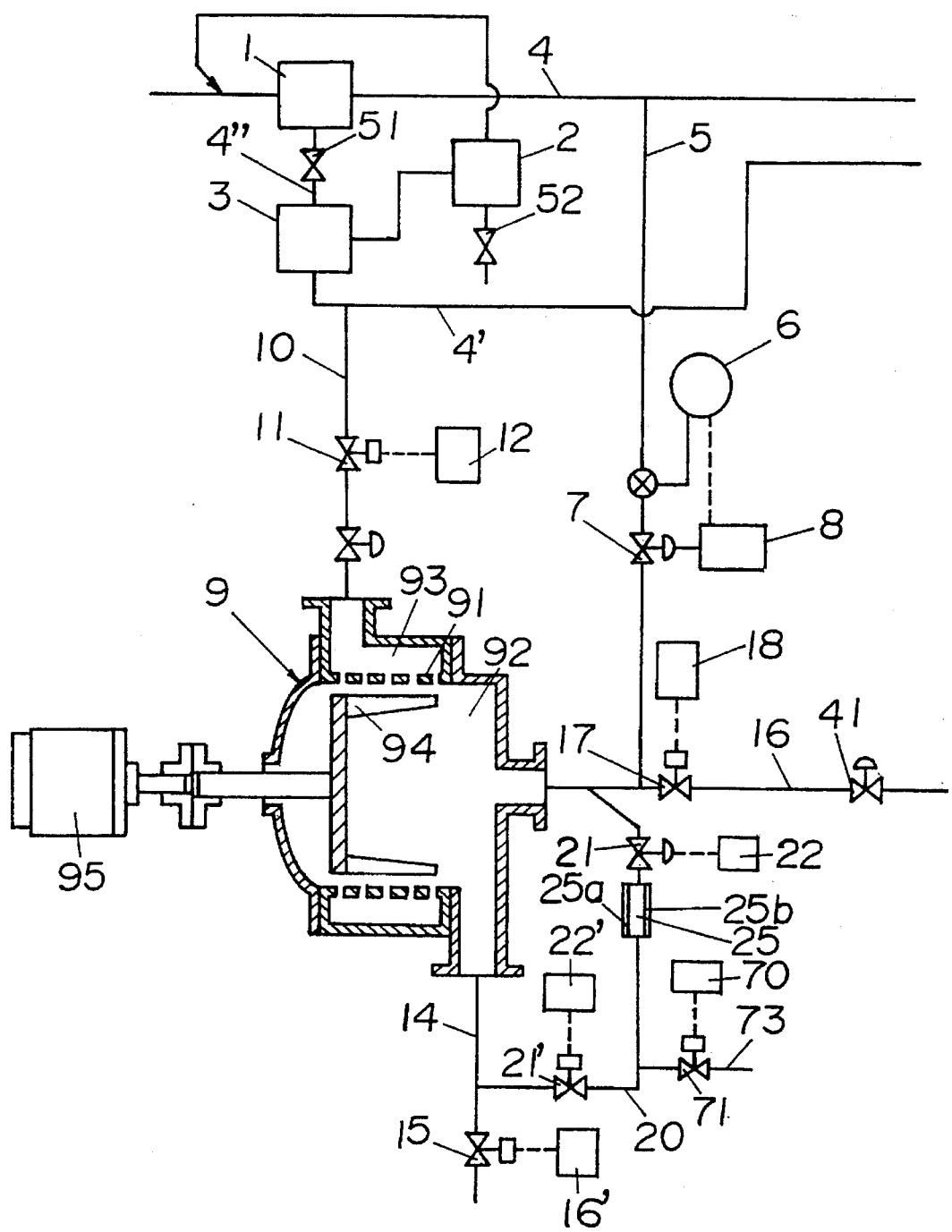
FIG. 4 is a schematic view explaining a device for detecting foreign matter in pulp suspension of another embodiment according to the present invention.

Still further, the present embodiment describes a device for detecting foreign matter in pulp suspension comprising the pulp suspension passage 4 for introducing the pulp suspension; the pulp suspension introducing passage 5 connected at one end to the pulp suspension passage 4 for introducing the pulp suspension; the separating means 9 connected to the other end of the pulp suspension passage 4 for separating the pulp suspension which is introduced from the pulp suspension passage 4 into foreign matter and effective fiber; the inspecting section 25 for inspecting foreign matter separated by the separating means 9; and the detecting means 32 for detecting foreign matter in the inspecting section 25. However, the present invention is not restricted to this embodiment. For example, as shown in FIG. 4, only the inspecting means 25 constructed to be able to externally distinguish foreign matter may be provided in lieu of the detecting means 32.

That is, the present invention may comprise the pulp suspension passage 4 for introducing the pulp suspension; the pulp suspension introducing passage 5 connected at one end to the pulp suspension passage 4 for introducing the pulp suspension; the separating means 9 connected to the other end of the pulp suspension passage 4 for separating the pulp suspension which is introduced from the pulp suspension passage 4 into foreign matter and effective fiber; and the inspecting section 25 constructed to be able to externally distinguish foreign matter separated by the separating means 9 (the inspecting means 25 are formed of, for example, two pieces of transparent glass 25a and 25b parallel to each other).

Figure 5:
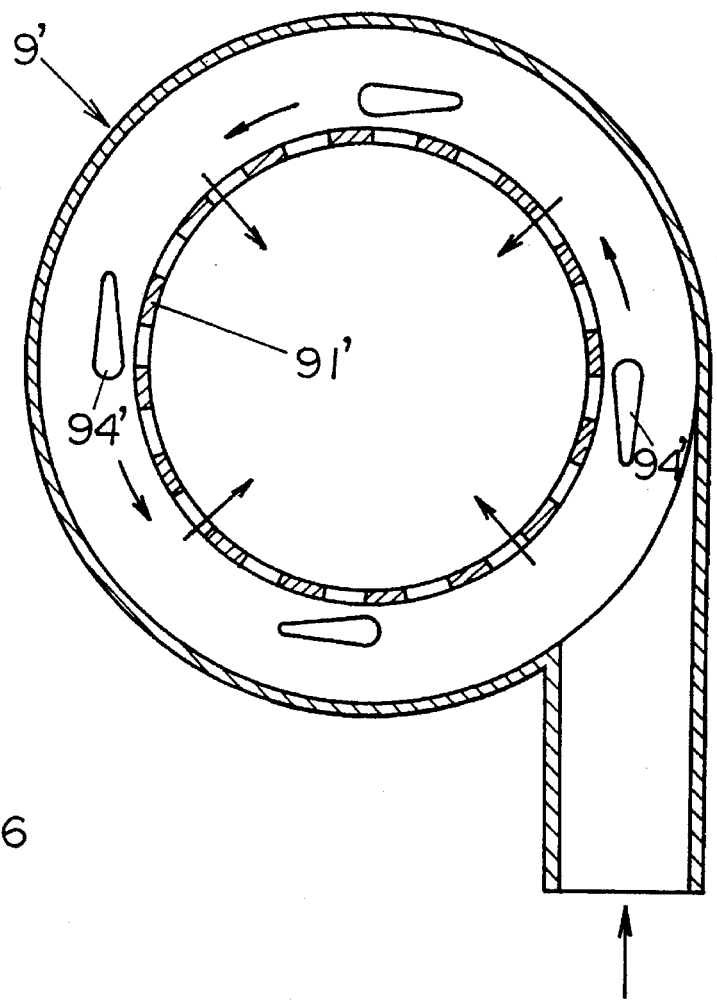
FIG. 5 is a sectional schematic view of an inward flow screen of one example of separating means used for a device for detecting foreign matter in pulp suspension of one embodiment according to the present invention.
Figure 6:
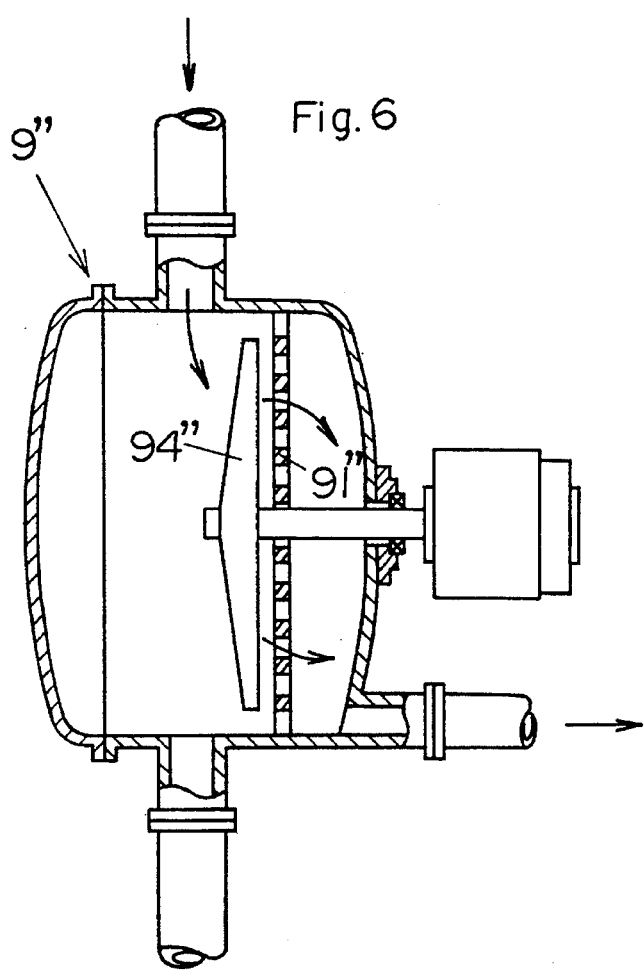
FIG. 6 is a sectional schematic view of a closed-type screen using a flat-type screen plate of one example of separating means used for a device for detecting foreign matter in pulp suspension of one embodiment according to the present invention.

In the present embodiment, the so-called outward flow screen is used for the separating means 9 such that the rotating member 94 is rotated inward (inlet) of the screen 91, thereby flowing the diluted pulp suspension from inward to outward of the screen 91 and screening it. However, the present invention is not restricted to this embodiment; but instead, some modifications may be made to the separating means 9 as follows. An inward flow screen 9' (See FIG. 5) may be employed such that a rotating member 94' is rotated outward (inlet) of a screen 91', thereby flowing the material from outward to inward of the screen 91' and screening it. Or, a closed-type screen 9" (See FIG. 6) using a flat-type screen plate 94", or a cleaner for separating foreign matter by utilizing centrifugal force and liquid shearing force may also be applicable. Also, in the present embodiment, when the pulp suspension is separated, it is preferably diluted with water. However, the present invention includes pulp suspension which may be separated without adding water, and thus, does not restrict the separating means.

As will be clearly understood from the foregoing description, the present invention offers the following advantages.

A method of detecting foreign matter in pulp suspension according to the present invention is employed whereby a certain amount of sampled pulp suspension is diluted by adding a certain amount of water, and the diluted pulp suspension is the object to be detected. Thus, foreign matter can be distinguished and detected easily even though the pulp suspension which will be sampled is highly concentrated.

Also, a method of detecting foreign matter in pulp suspension according to the present invention is employed whereby a certain amount of sampled pulp suspension is diluted by adding a certain amount of water, and the resulting pulp suspension is separated into foreign matter from effective fiber. Since the water containing separated foreign matter is the object to be detected, unlike the conventional pulp suspension per se, foreign matter can be distinguished and detected easily and reliably regardless of the concentration of the pulp suspension which will be sampled, and even though the pulp suspension material is waste paper, corrugated board, or the like.

A device for detecting foreign matter in pulp suspension according to the present invention is provided with an inspecting section which is constructed to be able to externally distinguish foreign matter separated by the separating means for separating the pulp suspension into foreign matter and effective fiber. Thus, the object to be distinguished is not the conventional pulp suspension per se, and consequently, foreign matter can be distinguished with the naked eye easily and reliably regardless of the concentration of the pulp suspension which will be sampled, and even though the pulp suspension material is waste paper, corrugated board, or the like.

Also, a device for detecting foreign matter in pulp suspension according to the present invention is provided with an inspecting section which is constructed to be able to externally distinguish foreign matter separated by the separating means for separating the pulp suspension into foreign matter and effective fiber and with detecting means for detecting foreign matter inspected in the inspecting section. Thus, the object to be detected is not the conventional pulp suspension per se, and consequently, foreign matter can be distinguished and detected easily and reliably regardless of the concentration of the pulp suspension which will be sampled, and even though the pulp suspension material is waste paper, corrugated board, or the like.

Further, in a device for detecting foreign matter in pulp suspension according to the present invention, the sampled pulp suspension is diluted by adding water from the water-supply passage, and the diluted pulp suspension is separated into foreign matter and effective fiber, thus circulating the water containing separated foreign matter in the circulation passage and averaging it. Hence, since the object to be detected is not the conventional pulp suspension per se, but the averaged pulp suspension, foreign matter can be distinguished and detected easily and reliably regardless of the concentration of the pulp suspension which will be sampled, and even though the pulp suspension material is waste paper, corrugated board, or the like.

Still further, in a device for detecting foreign matter in pulp suspension according to the present invention, the effective fiber and foreign matter of the sampled pulp suspension are discharged from the discharge passage and the foreign-matter discharge passage, respectively, and consequently, the pulp suspension to be newly sampled is introduced into the separating means as a new object to be detected by opening the introducing-passage opening and closing means, thereby distinguishing foreign matter continuously.

What is claimed is:

1. An apparatus for detecting and determining the average value of foreign materials contained in pulp suspension, comprising:

a pulp suspension introducing passage for introducing pulp suspension containing foreign materials and pulp components, separating means including a primary chamber having an inlet connected to the pulp suspension introducing passage and an outlet, a secondary chamber situated adjacent to the primary chamber and having an outlet, and a screen separating the first and second chambers so that when the pulp suspension is introduced into the separating means through the primary chamber's inlet, the pulp components in the pulp suspension pass through the screen and the secondary chamber to exit from the secondary chamber's outlet and the foreign materials remain in the primary chamber, a circulation passage connected between the primary chamber's inlet and the primary chamber's outlet for circulating the pulp suspension containing the foreign materials in the primary chamber therethrough so that the pulp suspension containing the foreign materials separated in the primary chamber substantially circulates through the circulating passage, and means for detecting and determining the average value of the foreign materials contained in the circulated pulp suspension, said detecting means being located in the circulation passage so that the foreign materials contained in the pulp suspension after the pulp components are removed in the separating means are detected while the liquid is circulating in the circulating passage to thereby accurately detect the foreign materials in the pulp suspension.

2. The apparatus according to claim 1, further comprising water supply passage connected to the inlet of the primary chamber so that the foreign materials are diluted and suspended in water.

3. The apparatus according to claim 2, wherein said separating means further includes a rotating member situated inside the primary chamber to prevent the screen from being clogged.

4. The apparatus according to claim 3, further comprising a discharge passage connected to the primary chamber's outlet for discharging the foreign materials after detection.

5. The apparatus according to claim 4, further comprising opening and closing means situated in each of the pulp suspension introducing passage, circulating passage and discharge passage for controlling flow of the passages.

* * * * *